United States Patent [19]

Mandel et al.

[11] Patent Number: 4,893,935

[45] Date of Patent: Jan. 16, 1990

[54] APPARATUS AND METHOD FOR OPTICAL DENSITY MEASUREMENTS OF BIOMASS PROCESSES

[76] Inventors: William R. Mandel, 122 B Avenida Dr., Berkeley, Calif. 94708; Anthony J. Dekovich, 14930-C Reedley St., Moorpark, Calif. 93021

[21] Appl. No.: 234,367

[22] Filed: Aug. 19, 1988

[51] Int. Cl.$^4$ ............................................. G01N 21/00
[52] U.S. Cl. ..................................... 356/436; 356/442; 435/291
[58] Field of Search ............... 356/441, 442, 436, 440; 435/291

[56] References Cited

U.S. PATENT DOCUMENTS

| | | | |
|---|---|---|---|
| 3,714,445 | 1/1973 | Blachere et al. | 435/291 |
| 3,727,066 | 4/1973 | Louderback et al. | |
| 3,819,278 | 6/1974 | Muller | |
| 3,962,041 | 6/1976 | Muller et al. | |
| 4,021,120 | 5/1977 | Muller et al. | 356/442 |
| 4,561,779 | 12/1985 | Nagamune et al. | |
| 4,577,110 | 3/1986 | MacBride et al. | |

FOREIGN PATENT DOCUMENTS 0210869 4/1987 European Pat. Off. .

OTHER PUBLICATIONS

Monk et al., Measurement of Yeast Growth . . . , J. Gen. Appl. Microbiol, 29,467-2/75, (1983).
Lee, Y. H., Biotech and Bioeng, vol. XXIII, pp. 1903-1906, (1981).

*Primary Examiner*—Leon Scott, Jr.
*Attorney, Agent, or Firm*—James R. Cypher

[57] ABSTRACT

This invention relates to an apparatus, method and system for directly obtaining the optical density of a dynamic biological system over the wide operating range and a wide range of organism mass, compensating for the primary interference factor, agitation and gas bubble formation, and thereby obtaining a on-line real time monitoring of cell density to follow the product concentration and progress of the biological reaction system.

8 Claims, 3 Drawing Sheets

APPARATUS AND METHOD FOR OPTICAL DENSITY MEASUREMENTS OF BIOMASS PROCESSES

BACKGROUND OF THE INVENTION

The present invention relates to an improvement in or relates to an apparatus and method for obtaining optical density measurements as a means for accurately monitoring a dynamic biomass process system, such as a fermentation, anaerobic or aerobic microorganism process. More specifically, this invention relates to a method for determining the direct optical density of a dynamic process system over the entire operating range by compensation for the primary interference factor.

The measurement of cell density is important in monitoring the program of a fermentation process. There have been numerous methods and accompanying apparatus for measuring cell density. None of the previous methods and apparatus have proved successful and satisfactory before the present invention. Preferably, the use of a sterilizable probe, which can be inserted directly into the fermentor or nutrient media for measurement of the cell density, would be desirable and provide valuable information in monitoring the progress of the process. Normally, product concentration is associated with the cell mass derived from the cell density measurements.

Heretofore, the cell density is measured in discrete intervals by withdrawing samples from the fermentor. This procedure could not produce direct and rapid measurement of the product, but resulted in an estimation of cell mass which was an indication of product concentration at the time the sample was withdrawn from the fermentor. To accomplish satisfactory and accurate process control utilization of a direct measurement system, an on-line measurement system is desirable.

Indirect control measurements are based on various process parameters and are limited by the accuracy of the mathematical model of cell growth, substrate consumption and product formation. Assumption of constant yields, maintenance coefficients, and stoichiometry may not be valid over the entire process range due to depletion of substrates, an accumulation of intermediates which may become metabolized and formation of inibitory products.

In the discrete interval method of cell density measurement at best this is a density approximation technique. From a sterilized sample port, a small volume of culture broth is withdrawn, after assurance the port has been purged. The sample is transported to the laboratory bench and the appropriate dilution of the sample made. Special attention must be paid to accuracy and consistency of the pipetting technique and equipment as between other operators also taking interval samples. Finally, the optical density is measured, multiplied by the dilution factor and the value recorded. During this time, from sample collection to value recording, it is unknown which next appropriate process step is necessary to optimize the overall process.

The discrete interval method of cell density measurement is not conducive to automation. Reliance must be on some indirectly measured parameter: metabolic or physical. Measurements in dynamic systems present various drawbacks. The physical complexity of microbial fermentation cultures is affected by characteristics of the media, the size, shape and type of the organism; changes in the process: pH, temperature, pressure, agitation and the like. Metabolic complexity of growth cultures is influenced by phases of microbial growth in response to the physical environment. This affects cell size, replication duplexes, chain formation, inclusion, body formation and the like. Also for microbes growing in complex nutrient broth, it is not certain which nutrients are utilized at each stage of development in the process. Hence, it is difficult to prepare a model of the growth.

Heretofore, optical sensors would be favorable for measurement of the amount of light that passes through a process fluid. However, the amount of light transmitted through any particular process fluid can be diminished by various factors, such as, suspended solids, dissolved solids and emulsion formation. Suspended solids and emulsions reduce light transmittance by light scattering, as well. In an aerobic system the optical density appears to be influenced by the number of bubbles and their size. Large gas bubbles, such as air bubbles, scatter light just as large particles, but still retain some light transparency. At higher agitation speeds, where smaller bubbles are produced, the scattering of light has a lessened effect, and transparency is increased. Therefore, a biomass system has inherent problems associated with optical sensor measurements.

OBJECTS OF THE INVENTION AND SUMMARY OF THE INVENTION

It is therefore the object of the present invention to provide an apparatus and method for direct optical density measurement of a dynamic biomass process system in which organisms are growing, wherein rapid direct measurements of cell density are required; the measurements are made on-line or real-time with respect to the process; in-place measurement is used to avoid problems associated with incremental discrete sampling such as the logistics of obtaining the interval sample, sterilization, risk of disturbing the process, time lapse from taking of a sample to recording of the measurement, rapid determination of appropriate process step at the incident time of sampling.

Another object of this invention is to provide a method for determining the concentration of an aerobic or anaerobic biomass system in terms of optical density compensating for any interfering factor, such as gas bubbles, assuring linearity of the measurement over its full range.

Another object is to provide an optical density measurement apparatus which facilitates automatic on-line real time monitoring of fermentation process resulting in full automation of the process.

A general object of the present invention is to overcome the disadvantages of the prior art. Yet further objects will become apparent hereinafter in the detailed description which follows.

These objects are achieved in the present invention by the utilization of a sterilizable fiber optic probe having a cell opening or path length through which reacting biomass fluid passes; and having a fiber optic light source and fiber optic light detector. When in operation the light from the light source fiber optic passed through the sample media in the cell opening and the transmitted light is then sent through the receiving end of the fiber optic line and sent to the transmitter; said transmitter consists of a signal amplifier and a computer program to linearize the signal output. The optic probe is removably sealed into a fermentor vessel or similar unit with control instrumentation.

In general, the optical sensor in the probe measures the amount of light that passes through a process fluid present in the cell opening. The system is capable of automatically compensating for the presence of gas bubbles in the cell opening.

DETAIL DESCRIPTION OF THE INVENTION

Figure 2:
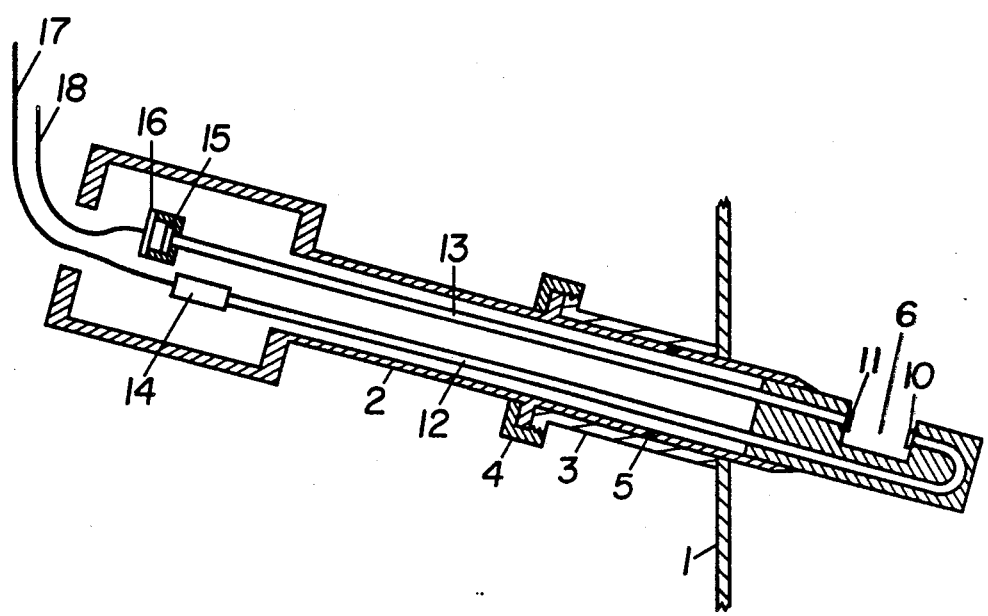
FIG. 2—Schematic of the probe with measuring cell.

Referring to the drawings, and in particular to FIG. 2, the reference numeral 2 indicates a probe in accordance with the invention. The probe 2 can be made of any non-corrosive material relative to the media in the processor. However, preferably the probe 2 is made of stainless steel construction. The probe consists of an Ingold fitting 4 which allows the probe 2 to be inserted into the body or wall of a reactor 1, such as a fermentor tank, and to be removably securably fitted thereto. The Ingold fitting 4 and an o-ring assembly 5 allows the probe 2 to be sealably fitted through an access tube 3 connected to the wall of the reactor 1 and the acces tube 3 has the cooperating connecting fitting of the Ingold fitting 4.

Within the probe 2 there is a radiation light source 14 and sensing photo detector 16. Each of the respective light source 14 and the detector 16 are connected to electrical conductors 17 and 18, respectively. The light source 14 is supplied with current by conductor 17. The detector 16 transmits a signal impulse through current conductor 18 to a means for amplifying and recording the signal. The radiation light source 14 and photo detector 16 are removed from the process media by use of fiber optics 12 and 1, which are used to transmit the source light 12 and to transmit the detected light 13. The cell opening in the end of the probe protruding into the reactor and reaction media therein, there is defined by a path length a sample gap 6 in which the fiber optics 12 and 13 terminate in are windows 10 and 11 sealed in place. The windows 10 and 11 are the terminal portions of the respective fiber optics 12 and 13 and act to protect the ends of the optic fibers. The windows 10 and 11 generally face each other in the sample gap 6. Further, these windows 10 and 11 can made of any light transmissive material which will allow the needed light radiation therethrough into the sample gap 6, and similarly, detection of the transmitted light through the material present in the sample cell 6. Preferably, the windows are made of Pyrex or quartz.

The pick up fiber optic 13 is connected to a photo detector 16 which in turn is connected to a current conductor 18. Covering the photo detector is an optical filter 15 which removes all the light wavelengths below 850 nanometers, thus removing ambient light interference. The filter wavelength cut-off also removes interference from color. Hence most particles appear similar at this higher wavelength.

During the process the solution in the fermentor vessel begins as an almost clear broth solution and proceeds during the process to a very dark solution. An optimal optical path length is selected in the sample gap 6 which allows the probe to see over the entire range of the process. The measurement range is inversely proportioal to the path length and resolution is directly proportional to path length. Hence, the smaller the path length in the cell 6 of the optic probe the greater the observable range, but the smaller the resolution.

The typical unit of measurement is the absorption unit (A.U.). This is an arbitrary unit which is defined in use as—zero A.U. is the amount of light absorbed in a clear nutrient medium in the absence of cell growth. Each additional unit is one decade change (factor of 10, i.e. log change) of the amount of light absorbed and is correlated to the current output by the photo detector.

Figure 1:
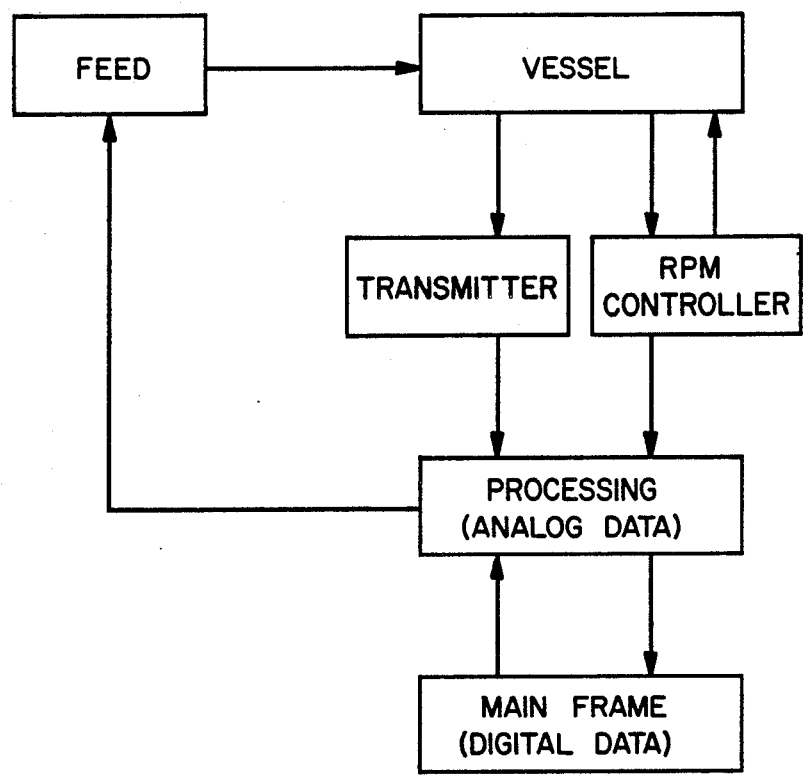
FIG. 1—Schematic diagram of the entire process system.
Figure 3:
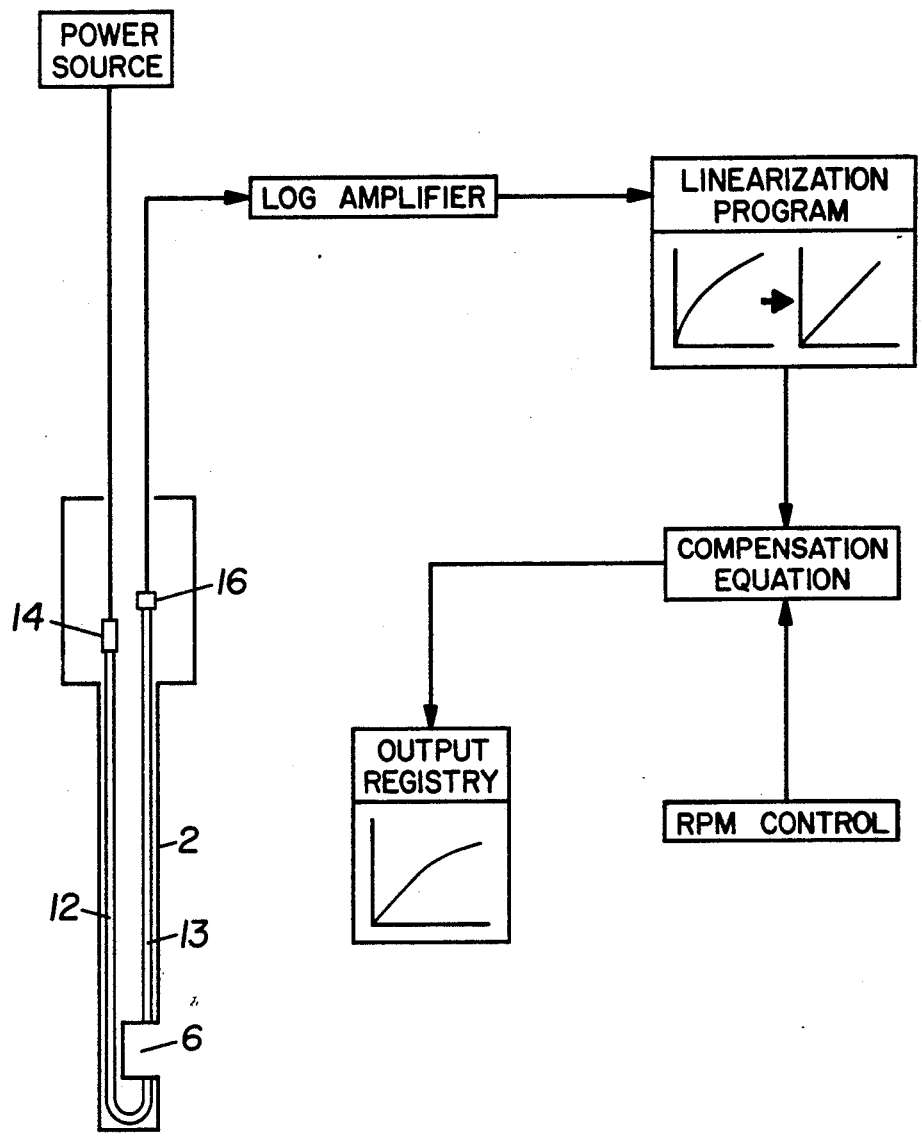
FIG. 3—Schematic of a biological system reactor-fermentor.

One problem that results in such a system is the correlation between light absorption readings and the actual concentratio measurement may not be linear over the entire range. In any infinitely small segment in the absorption curve, there is a linear relationship of process to photo output. But in the case of a large range measurement a linear relationship does not exist, meaning a change in a clear region does not reflect an equal or equivalent change in the dark region. However, this imbalance or non-equal change can be linearized in the programed transmitter FIG. 2 AND FIG. 3. The transmitter is a microprocessor controlled transmitter with a numeric key pad entry source and a character display. Therefore, by understanding the behavior relationships between particles and knowing certain phenomenon about the nature of light in relation to concentration, it is possible to extrapolate an accurate linearized curve from only two entered points.

When a standard microbial fermentor fitted with necessary control instrumentation was used, the internal arrangement within the fermentor is a series of baffles oriented radially and a heat exchange unit. The baffles prevent vortexing to improve aeration efficiency. Also used is a means for efficiently dispersing small bubbles into the medium, such as three disk turbine impellors placed on the fermentor agitator shaft. A combination orifice sprayer/impellor (perforated pipe) generates and disperses small air bubbles throughout the fermentor. Speed of agitation, which is variably adjustable to 1000 r.p.m., was provided in the fermentor.

The function of agitation is to increase the area available for oxygen transfer by dispersing the air in the culture broth in the form of small bubbles. Agitation also delays the escape of air bubbles, i.e. increases the residence time, from the liquid and prevents coalescence. Agitation decreases the thickness of the liquid film at the gas/liquid interface by creating turbulence in the culture field. In general, this equipment as described is very efficient in generating a large number of tiny gas bubbles in the fermentor.

In the above-defined aerobic fermentation system the agitation rate (turbulence) is the principle interference factor in obtaining accurate and representative cell density measurements. Air flow rate and air pressure have a small effect. The problem of uncontrolled foaming is caused by increased bubble residence time. As foaming continues there is a quantitative increase in the size and number of bubbles.

The stainless steel probe is removably and sealably affixed through the side of the fermentor, so that the sensing portion of the probe containing the light source optic fiber, photo detector optic fiber and density measurement cell is directly inserted into the fermentation media. As the fermentation progresses the liquid media solution can range from an almost clear solution to a very opaque solution. An optical path is selected in the probe to allow the probe to sense the entire range of the process. In the case of large range measurements the correlation between observed and actual measured values may not be linear. This means that a change in the clear region does not reflect or indicate an equal change in the opaque region. Hence, the probe is coupled to a transmitter which is programed to linearize the measurements over a large range.

It has been discovered that the rate of agitation has an effect on the observed on-line cell density. The change in signal from the probe has been found to be proportional to the agitation rate and inversely proportional to the cell density. Therefore, the probe signal is a composite value which depends upon: (a) cell density and solution viscosity, (b) agitation rate if greater than 400 r.p.m., and (c) the size and number of bubbles in the liquid media.

The correction Model, which adjusts the raw density data, is based on two straight-line equations. Each equation which correlates the on-line cell density value to optical density at a particular agitation speed (r.p.m.). The intersection of the straight-line equations is a point where agitation has no affect on the signa. That is, below this point an increase in agitation makes the solution look darker, i.e. more opaque (higher optical density), influenced by the number of bubbles and their size; and above this point, an increase in agitation makes the solution look lighter (lower optical density). The phenomenon is attributed to the effect of the bubbles in the media to the overall signal from the probe. That is, at this point the transparent effect equals the scatter effect due to the presence of bubbles in the fermentation media.

Another factor incorporated into the linearization equations is the known effect of agitation rate on the bubbles. It was found that at other than the crossover point there is a nonlinear correlation between r.p.m.'s and signal changes. An equation is selected that best approximates the phenomenon between 200 r.p.m. and 1000 r.p.m. Little or no aeration occurs below 200 r.p.m., and similarly little or no aeration occurs above 1000 r.p.m., where the aeration process begins to level off due to the general process and equipment design limitations.

The probe signal was found to be a factor of the agitation rate. Response also is dependent on the relative cell to air bubble concentration as compared to the rate of agitation. That is, under the same conditions, at low cell densities the signal is greater at high agitation rates than it is at high cell densities. A curve in the low agitation region was selected for the greatest accuracy in the range that was most critical for the fermentation process. A polynomial derivation of the curve was determined from the data collected from the effect of agitation rate on the signal strength at a given or selected optical density. The curve was in the form Percent optical Density
change = $k_0 + k_1 Ag + k_2 Ag^2 + k_3 Ag^3$ where k is a constant and Ag is the agitation rate. The transmitter generates a response curve which closely approximates the phenomenon, i.e. a linear change in the concentration range, and adjusts the curve to fit the actual process fluid.

The transmitter generates the response curve by taking readings on-line or in sample containers, storing the readings in memory and the stored readings are assigned values that have been determined in the laboratory.

The instrument system uses a programed computer which measures the concentration or consistency of a fluid by light absorption. Said programed computer monitors a process continuously and outputs a value consistent with the process standardization curves. At a minimum, a two-point standardization curve is required to linearize the output. Thus, off-line sampling and laboratory errors are reduced and the result is representative of the real-time concentration of the fluid.

The programed computer is a microprocessor based digital instrument with a modular design, consisting of circuit boards, analog output boards, central processing board to run the program which includes the electronics and interprets the measurement data, digital communication board, front panel board for human interface, lamp output board to set the prope voltage for sensor lamps with line voltage loss compensation; a mother board to interconnect all the boards to form the integrated instrument system. Power supply provides regulated and unregulated supply for the circuitry, relays and sensors; sensor input board which conditions a sensor signal to standardize the input for microprocessor readability.

In operation the microprocessor can interpret and display measurements from a variety of sensors. In general, optical sensors measure the amount of light that passes through a process fluid. The amount of light transmitted can be diminished by suspended solids, dissolved solids, and emulsions, as discussed hereinabove. Suspended solids and emulsions also reduce light transmittance.

As mentioned hereinabove, the typical unit of measurement is the arbitrary A.U. (absorption unit). A.U. is defined in use as, zero A.U.—the amount of light absorbed in a clear (or zero) solution. Each additional unit is one decade change in the amount of light absorbed and hence can be correlated to the current output by the photo detector. As an example, zero A.U. may be of 10 mA of current output by the photo detector, 1 A.U. then would be 1 mA and 2 A.U. would be 0.1 mA of output and so forth.

The problem the instant invention overcomes is the correlation between light readings and the actual cell density measurements, which may not be linear. In any small segment in the resulting curve there is a linear relationship between process cell density and photo output. But over a larger range a linear relationship does not exist; particle behavior in clear media does not correlate to an equivalent behavioral change in the dark or opaque region. This is linearized in the transmitter by the programed microprocessor.

Thus, the disadvantages of the prior methods are eliminated. An improved direct estimation system has resulted in more accurate and rapid determinations of cell density in fermentors and similar reactors. Even in the turbulent environment of a fermentor with the presence of bubbles from the aeration or the reaction taking place in the reactor, it has been possible with the present invention to directly resolve cell densities in excess of 100 OD and to couple the system directly to a computer system for process control.

It will be understood that each of the elements described above, or two or more together, may also find a useful applications in other types of constructions, systems and the like, which differ from the types described above.

While the instant invention has been illustrated and described as embodied in measuring the turbidity of a liquid in which micro-organisms are growing, it is not intended to be limited to the details shown and described, since various modifications and structural changes may be made without departing in any way from the spirit and scope of the present invention.

Without further analysis, the foregoing will reveal the gist of the present invention, that others skilled in the art to which it pertains by applying current knowledge, can readily adapt it for various applications without omitting features that, from the standpoint of prior art, fairly constitute essential characteristics of the generic or specific aspect of this invention.

What is claimed is:

1. A method for monitoring a dynamic biological system in a biological reactor containing developing culture fluid media, by measuring the transmitted light in a defined cell, the steps which simultaneously comprise:
    (a) irradiating fluid media in the cell;
    (b) continually agitating the culture fluid media;
    (c) detecting the transmitted light;
    (d) converting the detected transmitted light to a non-linear electrical output signal;
    (e) linearizing said non-linear electrical output signal;
    (f) compensating said linearized output signal for the effect of agitation; and
    (g) recording the signal.

2. The method of claim 1 in which said monitoring of a dynamic biological system is by measurement of a direct optical density of said developing culture fluid media in the cell.

3. Apparatus for measuring direct optical density of a liquid biological media in a biological reactor in which said liquid media is agitated, said liquid media containing developing and growing biological species, comprising means for projecting an optical probe having a sensing cell into said liquid biological media said probe having oppositely positioned light source and light detector within said cell, and having connected to said light detector external to said reactor means for linearizing said detector output signal and means for compensating said output signal for interference caused by agitation of the liquid media in the reactor; and means for recording the results of the optical density in the cell.

4. The apparatus of claim 3 wherein said means for projecting said probe having an optical sensing cell into the liquid biological media is a probe having fiber optics carrying the light to the cell and oppositely positioned thereto a photo sensitive detector attached to fiber optics to carry the signal to an external amplifier and recorder.

5. A method for determining cell mass of a biological system by performing a curve fitting calculation on optical density data and agitation data from a biological reactor containing developing culture fluid, comprising the steps of:
    selecting at least two sets of rates of agitation and corresponding optical density by, linearizing the results in a transmitter by a programed microprocessor and defining the value of the cell mass as a function of the agitation and optical density and compensating for the effect of agitation by two straight line equations each of which correlates the on-line cell density density value to optical density at a particular agitation rate, thereby relating the cell mass to optical density.

6. The method of claim 5 wherein the linearization is the determination of at least two slopes of said straight line equations for the linear relationship between two sets of at least two points each for rates of agitation and corresponding optical density.

7. The method of claim 6 wherein the step of linearization is based on two separated points at least twenty percent of the zero to span apart, and other than zero, wherein zero represents a background fluid in the biological reactor.

8. The method of claim 5 wherein an agitation rate is selected as a constant value determined by the need of the developing cells for oxygen in the biological reactor containing developing culture fluid.

* * * * *